United States Patent [19]
Kannenberg et al.

[11] Patent Number: 5,871,481
[45] Date of Patent: Feb. 16, 1999

[54] TISSUE ABLATION APPARATUS AND METHOD

[75] Inventors: Donald P. Kannenberg, San Jose; Scott P. Huntley, Danville; John N. Hendrick, San Jose, all of Calif.

[73] Assignee: Vidamed, Inc., Fremont, Calif.

[21] Appl. No.: 833,982

[22] Filed: Apr. 11, 1997

[51] Int. Cl.$^6$ .................................................. A61B 17/39
[52] U.S. Cl. ................................ 606/34; 606/41; 607/99; 607/105; 607/113
[58] Field of Search .................................. 606/32, 34, 41, 606/45, 49; 607/99, 100, 105, 113

[56] References Cited

U.S. PATENT DOCUMENTS

| | | |
|---|---|---|
| 2,008,526 | 7/1935 | Wappler et al. . |
| 2,038,393 | 4/1936 | Wappler . |
| 4,016,886 | 4/1977 | Doss et al. . |
| 4,474,174 | 10/1984 | Petruzzi . |
| 4,524,770 | 6/1985 | Orandi . |
| 5,370,675 | 12/1994 | Edwards et al. . |
| 5,385,544 | 1/1995 | Edwards et al. . |
| 5,484,400 | 1/1996 | Edwards et al. . |
| 5,540,681 | 7/1996 | Strul et al. . |
| 5,562,720 | 10/1996 | Stern et al. ................................ 606/32 |
| 5,651,780 | 7/1997 | Jackson ..................................... 606/34 |
| 5,728,143 | 3/1998 | Gough et al. .............................. 606/41 |

OTHER PUBLICATIONS

Greenwald Surgical Company, Inc., "Orandi ResecYoscope Injection Needle for Injection of Local Anesthetics," (Undated) Sheet No. P000121.

E.F. Nation, M.D., "Evolution of Knife–Punch Resectoscope," (Apr. 1976) Urology, vol. VII, No. 4. pp. 417–427.

R. Gutierrez, "Transurethral Treatment of Bladder Neck Obstructions: Endoscopic Prostatic Resection," (Apr. 1933) History of Urology, vol. II, Chapter V, pp. 137–186.

C.W. Ogden, Heat and the Prostate from Electrolysis to Microwaves: Lessons from an Historical Perspective, (Undated) Abstract, 2 sheets, p. 366.

Graversen, et al., "Transurethral incisions of the prostate under local anaesthesia in high–risk patients: a pilot study," (1987) Abstract, HealthGate Home Page, p. P000115.

Miller, et al., "Intergrated cystoscope: first rigid multipurpose operating cystoscope for local anesthetic endoscopy," (1989) Abstract, HealthGate Home Page, p. P000116.

(List continued on next page.)

*Primary Examiner*—Lee Cohen
*Attorney, Agent, or Firm*—Flehr Hohbach Test Albritton & Herbert LLP

[57] ABSTRACT

A radio frequency tissue ablation apparatus for use on a horizontal support surface in connection with a medical procedure on a patient. A portable carrying case having a carrying handle is provided and is adapted to rest upon a horizontal surface. The portable carrying case has a cover with an inner surface and is movable between a generally vertical open position and a generally horizontal closed position when the portable carrying case is resting on the horizontal support surface. The portable carrying case has a keyboard and a primary display panel disposed adjacent the keyboard under the cover when the cover is in a closed position and is accessible visually and physically when the cover is in an open position. The primary display panel includes a plurality of groups of numerical indicia and a plurality of switches associated with at least certain of the groups of numerical indicia for establishing criteria for those certain groups of numerical indicia. The primary display panel includes an additional switch for selecting automatic or manual operation. A graphic display panel is carried by the inner surface of the cover. Electrical circuitry, including a radio frequency generator and a control computer, is disposed within the portable carrying case and is coupled to the keyboard, the primary display panel and the graphic display panel. The portable carrying case has a plurality of ports accessible externally in communication with the electrical circuitry in the portable carrying case. A probe is coupled to one of the ports carrying an electrode and is adapted to penetrate tissue.

21 Claims, 2 Drawing Sheets

OTHER PUBLICATIONS

Orandi, "Urological endoscopic surgery under local anesthesia: a cost–reducing idea," (1984) Abstract, HealthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. Patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 2., pp. P000191–P000195.

T. Kirwin, "The Treatment of Prostatic Hypertrophy by a New 'Shrinkage' Method," (Aug. 1934) J. Urology, pp. 481–494.

TISSUE ABLATION APPARATUS AND METHOD

BACKGROUND OF THE INVENTION

1. Field of the Invention

This invention relates to a radio frequency tissue ablation apparatus and method and more particularly to a radio frequency tissue ablation apparatus and method for use in the human body and particularly for the treatment of benign prostatic hyperplasia.

2. Description of the Related Art

Radio frequency tissue ablation apparatus and methods have heretofore been provided. Typically this has involved two pieces of equipment namely a radio frequency generator and a computer, typically a laptop computer. Although the radio frequency generators were provided with displays such displays were often difficult to read in certain light situations. In addition it was often difficult to differentiate between the parameters displayed. Although automatic and manual procedures were available, it was difficult to transfer from one procedure to another. In particular when transferring from automatic to manual, it was necessary to almost restart the procedure. Also in the prior radio frequency generation apparatus, it was often necessary to have an attendant along with the physician to operate the apparatus in performing the method. Also in prior radio frequency generators, it was possible to detect high impedances which automatically shut off the power making it necessary to restart the procedure if it was desired to continue the ablation process. There is therefore a need to provide a radio frequency tissue apparatus and method which overcomes these deficiencies.

OBJECTS OF THE INVENTION

In general, it is an object of the present invention to provide a radio frequency tissue ablation apparatus and method in which switching between automatic and manual operations can be readily and efficiently performed.

Another object of the invention is to provide a radio frequency ablation apparatus of the above character in which the radio frequency apparatus and the computer have been integrated.

Another object of the invention is to provide an apparatus of the above character in which displays and controls are arranged in a more functional manner.

Another object of the invention is to provide an apparatus of the above character in which backlighting is utilized for the displays and controls.

Another object of the invention is to provide an apparatus and method of the above character in which it is possible for a single person to perform a procedure and to operate the controls.

Another object of the invention is to provide an apparatus and method of the above character in which impedance measurements are utilized for controlling functions.

Another object of the invention is to provide an apparatus and method of the above character in which the impedance is monitored to determine when a predetermined impedance is being reached and thereafter automatically producing the radio frequency power applied without the necessity of turning the power off.

Another object of the invention is to provide an apparatus and method of the above character in which when the power has been reduced because of impedance measurements power is thereafter applied at an appropriate level to avoid a high impedance condition.

Another object of the invention is to provide an apparatus and method of the above character in which high impedance conditions are only permitted to prevail for short periods of time.

Additional objects and features of the invention will appear from the following description in which the preferred embodiments are set forth in detail in conjunction with the accompanying drawings.

SUMMARY OF THE INVENTION

In general, the radio frequency tissue ablation apparatus for use on a horizontal support surface is comprised of a portable carrying case having a retractable carrying handle, the portable carrying case being adapted to rest upon the horizontal surface and having a top cover with an inner surface and being movable between a generally vertical open position and a generally horizontal closed position when the carrying case is resting on the horizontal support surface. The carrying case has a keyboard and a primary display panel disposed adjacent the keyboard and underlying the cover when the cover is in a closed position, the keyboard. The primary display panel and the keyboard are visually and physically accessible when the cover is in an open position. The primary display panel includes a plurality of groups of numerals and a plurality of switches associated with at least certain of the groups of numerals for establishing criteria for those certain groups of numerals and an additional switch for selecting manual or automatic operation. A graphic display panel is carried on the inner surface of the cover. Electrical circuitry is provided within the carrying case and includes a radio frequency generator and a control computer disposed within the case and coupled to the keyboard, the primary display panel and the graphic display panel. The case has a plurality of ports accessible externally in communication with the electrical circuitry. A probe forms a part of the apparatus and is coupled to one of the ports. The probe carries an electrode which is adapted to penetrate tissue.

DETAILED DESCRIPTION

Figure 1:
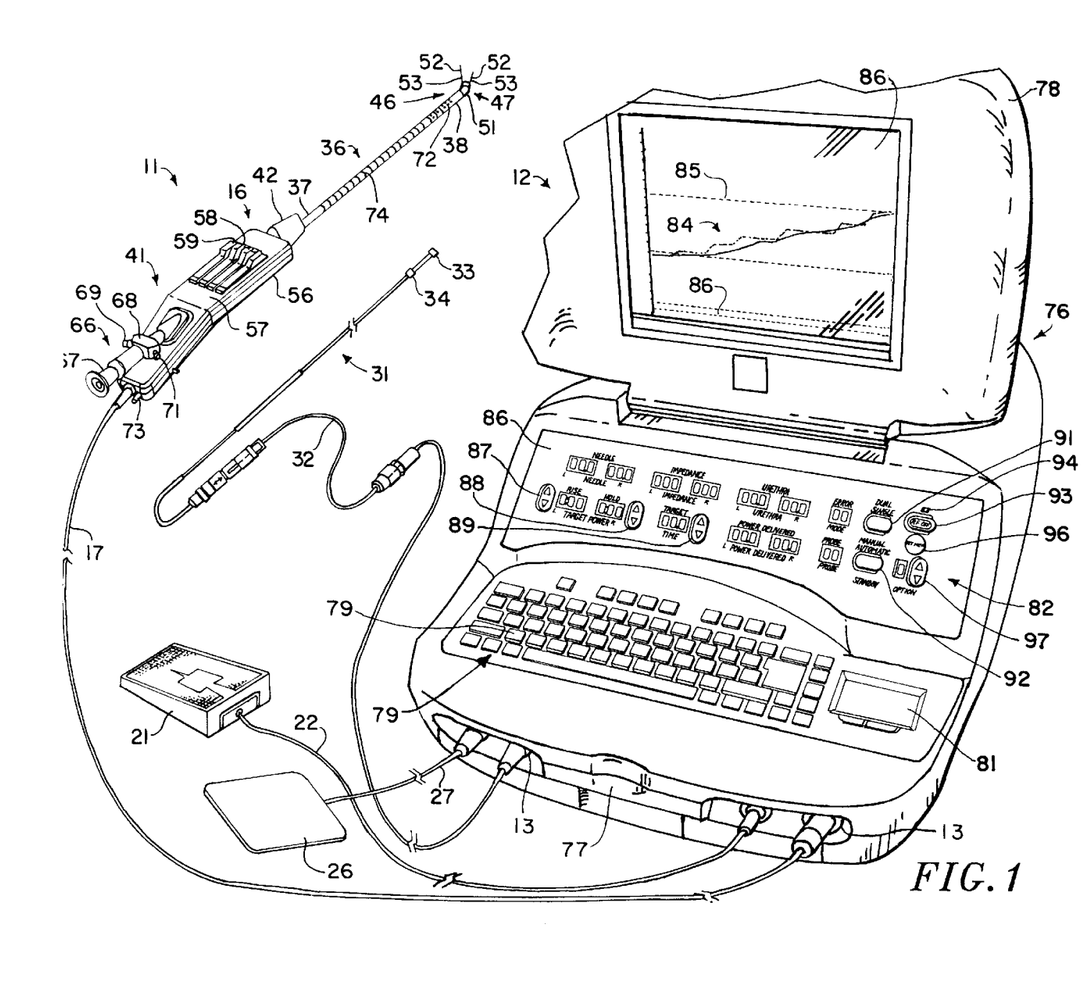
FIG. 1 is a perspective review of a radio frequency ablation apparatus incorporating the present invention utilized for performing the method of the present invention.

More specifically, the RF tissue ablation apparatus 11 incorporating the present invention as shown in FIG. 1 consists of a radio frequency (RF) generator and control console 12. The apparatus 11 also includes a probe 16 which is connected by cable 17 to one of the ports 13 of the console 12. It also includes a foot pedal 21 connected by cable 22 to another of the ports 13 of the console 12 having a plurality of external ports 13. A large area return electrode 26 is connected by a cable 27 to a port 13 of the console 12. A conventional rectal temperature monitoring device 31 may be included as a part of the apparatus 11 and can be connected to a port 13 of the console 12 by a cable 32. It includes first and second spaced apart thermocouples 33 and 34 which can be mounted on a flexible tape adapted to be inserted into the rectum of the patient.

The probe 16 can be of the type described in copending application Ser. No. 08/835,956 filed Apr. 11, 1997 and also of the type described in copending application Ser. No. 08/833,984 filed Apr. 11, 1997. As described therein, the probe 16 consists of a rigid elongate sheath 36 formed of a suitable material such as plastic. It is of a suitable size as for example 22-French and has a length of approximately 11" and is provided with proximal and distal extremities 37 and 38. The proximal extremity 37 of the sheath 36 is rotatably mounted on a handle 41 which is sized so as adapted to be grasped by an adult human hand. A knob 42 is provided on the proximal extremity 37 and is adapted to be grasped by a finger of the hand as for example the thumb to permit rotational movement of the sheath 36 for a purpose hereinafter described. The sheath 36 carries at least one and preferably first and second needle electrode assemblies 46 and 47 which are slidably mounted in the sheath 36 and which are directed through a transparent or clear rounded or bullet-shaped tip 51 in an off axis or a sidewise projecting positions at divergent angles with respect to each other as for example an angle ranging from 30–900. Each of the first and second needle electrode assemblies 46 and 47 consists of a conductive metal electrode 52 formed of a suitable material such as Nitinol and which is provided with a sharpened tip. A sleeve 53 formed of an insulating material is provided on each electrode and is slidably mounted with respect thereto so that predetermined lengths of the needle electrodes can be exposed in performing the radio frequency ablation as hereinafter described.

The handle 41 is formed of a two part case or housing 56 formed of a suitable material such as plastic. The housing 56 is provided with a flat upper surface 57 on which sliders 58 and 59 are mounted which are provided for controlling respectively the motion of the electrode 52 and the sleeve 53 of the first needle assembly 46 and sliders 61 and 62 are provided for controlling respectively the electrode 52 and the sleeve 53 of the second needle electrode assembly 47. The slider 58, 59 and 61 and 62 are adapted to be grasped by the thumb of the hand while the handle 41 is being held in the hand.

An optical viewing device 66 is slidably mounted in the handle 41 and is movable between the first and second positions and in the first position extending through the sheath 36 and through the transparent rounded tip 51 so that viewing of the region distally of the tip can be explored and a second position in which it is retracted into the sheath but being adjacent the transparent rounded tip 51 so that deployment of the first and second needle assemblies 46 and 47 can be observed.

The optical viewing device 66 includes an eye piece 67 through which viewing can occur. It also includes a fitting 68 which is provided with an adapter 69 which is adapted to be connected to a suitable source of light (not shown). It is also provided with another fitting 71 through which an irrigation liquid as for example a saline solution can be introduced. The liquid introduced passes through the sheath 36 and exits through the tip 51 into the tissue to be ablated to provide a clear field of view for viewing through the optical viewing device 66. The liquid introduced can be aspirated through a plurality of holes 72 provided in the sheath 36 and passing through the sheath and the housing 56 where it can be aspirated through an aspiration port 73 connected to a suitable source of vacuum. Spaced apart marks 74 are provided on the sheath to indicate to the physician performing the ablation procedure the length of deployment of the probe 16 into the urethra as hereinafter described.

The RF generator and control console 12 as shown in FIG. 1 is self-standing and consists of a portable carrying case 76 formed of a suitable material such as a molded plastic which is provided with the externally accessible ports 13. It is provided with a retractable carrying handle 77 and has a hinged cover 78 movable between an open position as show in FIG. 1 in which the cover extends in a generally vertical direction when the case 76 is resting on a flat or horizontal support surface as for example on a table and is movable to a closed position (not shown) in which it overlies a washable alpha-numeric QUERTY input keyboard 79 and a touch pad 81 adjacent the alpha-numeric input keyboard disposed within the case 76. It also overlies and covers up a primary display panel 82 disposed at an upwardly inclined angle to the rear of the keyboard 79. A liquid crystal display (LCD) panel 83 for the display of graphical information is mounted on the inside of the cover 78. The panel 83 can be used to display temperature impedance and power with respect to time in line graph 84 and be separated by splitter bars 85. These graphs can be adjusted in height. In addition, labels 86 can be provided on the panel 83 below the linegraphs 84 with digital values, as for example a specific needle and its temperature during an ablation procedure.

The primary display panel 82 consists of green light emitting diode (LED) displays for displaying numerical data in groups of numerical indices in the form of numerals. The display panel 82 is also provided with back-lit legends in the form of alphabetic indicia or letters as shown which are labeled from left to right respectively NEEDLE, IMPEDANCE, URETHRA above and below respective numeric displays and ERROR and MODE above and below respectively other numeric digits for the top row of numeric digits and RISE and HOLD above and TARGET POWER below, TARGET above and TIME below, and POWER DELIVERED above and below and PROBE above and below for numeric digits in the lower row of numeric digits. One set or group of three numeric digits is provided for the first or left (identified as "L") needle electrode assembly 46 and for the other or second set or group of three numeric digits for the second or right (identified as "R") needle electrode assembly 47. Each set or group of three digits features a tens and a units digit followed by a decimal point and a tenths digit. Under the designation URETHRA, there are provided two sets or groups of three digits each which are also used for measuring temperature in degrees Celsius in the same manner. This provides temperature readings from the thermocouples 33 and 34 carried by the rectal temperature monitoring device. Thus it can be seen that the green LED displays are grouped in pairs for the left and right needles and for the left and right urethral temperatures. The NEEDLE designation above these digits is lit in the manual mode of operation and the NEEDLE designation below these digits is lit for the automatic mode of operation.

Under IMPEDANCE there are also provided two pairs of three digits without any separators measuring load impedances in ohms. A display is provided for each of the left and right channels as shown. In the manual mode the top IMPEDANCE designation is lit and in the automatic mode the bottom IMPEDANCE designation is lit.

In the bottom row of indicators, time is displayed under RISE and HOLD for TARGET POWER with three digits appearing below each and featuring a single minutes digit followed by a colon and two seconds digits. It will display running time under the RISE category for the manual mode only and will display both rise and hold times for the automatic mode only. An up-down rocker switch 87 is provided on the left hand side of the RISE digits and an up-down rocker switch 88 is provided on the right hand side of the HOLD digits for setting the rise and hold times.

Continuing in the bottom row, a TARGET time is provided with three digits featuring a tens digit, a units digit followed by a decimal point and a tenths digit. A rocker switch 89 is provided at the right of the target digits to permit setting of the target time.

Next there follows a POWER DELIVERED indicia with two pairs or sets of digits representing the power delivered to the first and second channels associated with the first or left and second or right needle assemblies 46 and 47. Both pairs of digits display the power delivered to the left and right channels in watts and feature a tens digit, a units digit, a decimal point and a tenths digit. In the manual mode, the top POWER DELIVERED indicia is lit and in the automatic mode the bottom POWER DELIVERED indicia is lit.

In the same bottom row there are PROBE indicia having two digits which display the number of needle assemblies deployed. In the manual mode, the top PROBE indicia is lit and in the automatic mode the bottom PROBE indicia is lit.

In the top row underlying ERROR there are provided first and second indicators in the form of red LED's to indicate when an error or fault condition occurs. The ERROR indicia is also lit.

On the right hand side of the primary display panel 82 there is also provided a needle select button 91 having overlying back-lit indicia of DUAL and SINGLE to indicate that a single needle is being utilized for RF ablation as hereinafter described and when not lit dual needles are being utilized for RF ablation. A mode select button 92 having overlying indicia of MANUAL and AUTOMATIC is provided for selecting between manual and automatic operation. When the MODE select button 92 is lit, this indicates that automatic mode operation has been selected and conversely when not lit single mode operation has been selected. An RF OFF button 93 is provided at the far right hand side of the LCD panel 86 and is in red letters and is backlit when the RF energy is off. The RF OFF button underlies an RF on indicator 94. A SET MEMORY button 96 underlies the RF OFF button and is in blue and is utilized for setting lesion parameters to a value as displayed. The lesion parameters revert to default values at power on which means that the lesion parameters have to be set by the physician after the power has been turned on. A rocker switch 97 underlies the SET MEMORY button 96 and has associated therewith a green digit for displaying the selected nomogram selected by operation of the option rocker switch 97.

Thus, it can be seen that there has been provided a primary display panel 82 which includes a plurality of groups or sets of numerical indicia or numerals and a plurality of switches associated with at least certain of the groups or sets of numerical indicia for establishing criteria for those certain groups or sets of numerals. The display panel 82 also includes an additional switch, mode switch 92, for selecting manual or automatic operation.

A touch pad cursor control device 81 as shown is immediately adjacent to the QWERTY input keyboard 79 of a conventional type. It is operable with a latex-gloved hand and is compatible with both isopropyl alcohol and ammonia-based cleaners. It provides low to medium resolution (20–50 steps) or ⅛-direction control information.

Figure 2:
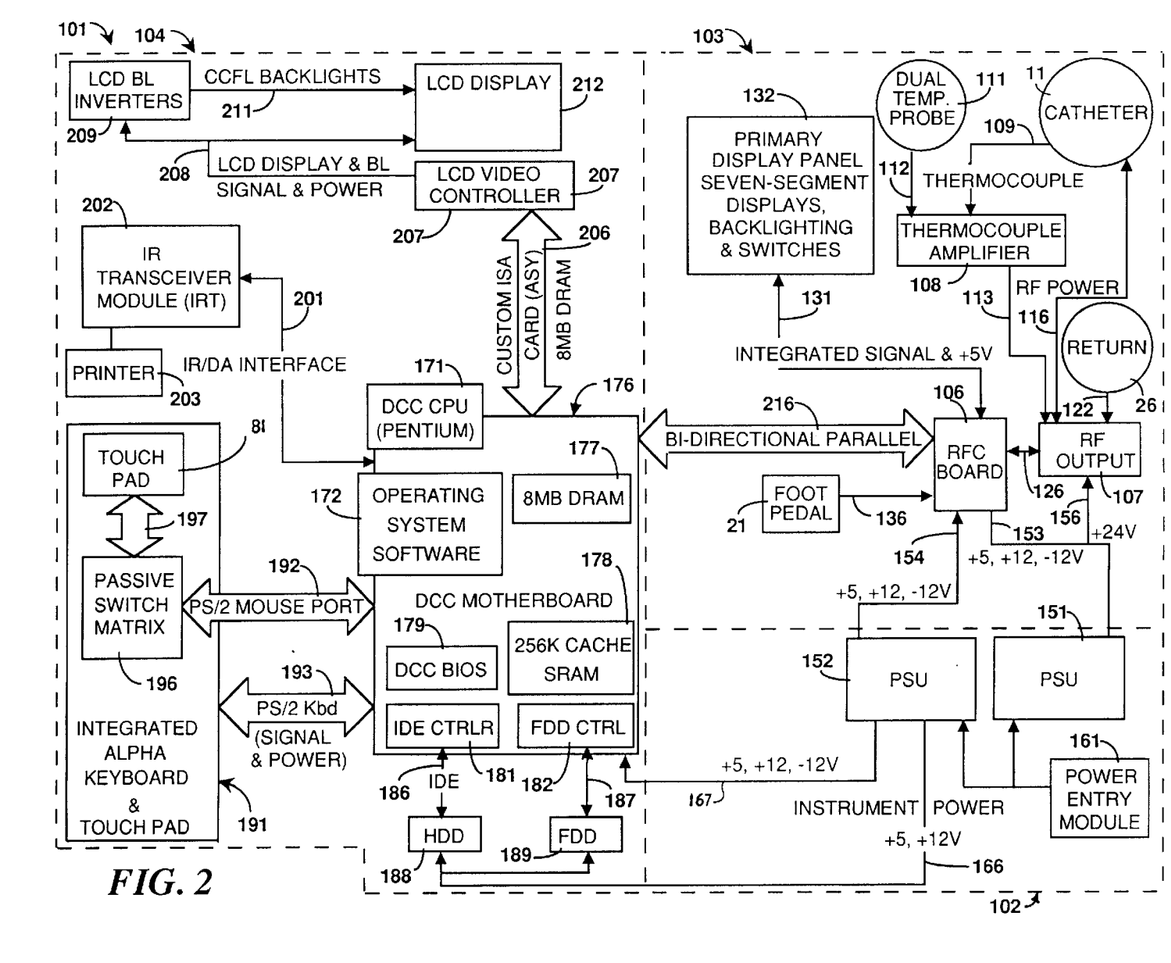
FIG. 2 is a block diagram of the electronic circuitry utilized in the apparatus shown in FIG. 1.

The RF generator and control console or carrying case 12 in addition to comprising the components hereinbefore described also includes electrical apparatus and circuitry 101 disposed within the carrying case 12 and is of the type shown in block diagram form in FIG. 2. The electrical and electronic circuitry 101 consists of an instrument power section 102, an RF generation and control section 103 and a display and recording section 104. The RF generation and control section consists of a radio frequency control (RFC) board 106 which is controlled by the foot pedal 21. The output from the board 106 is supplied to a radio frequency output block 107 which is comprised of two channels of radio frequency power ranging from 0 to 100 watts and preferably 0 to 50 watts per channel. The two channels of radio frequency power are supplied to the catheter or probe 11. The return path from the catheter or probe 11 is through the tissue of the human body through the return pad 26 to the radio frequency output block 107. The output from the RF output block 107 is controlled from a thermocouple amplifier 108 which is supplied with an input 109 which is connected to the thermocouple carried by the catheter as for example by the insulating sleeve of the catheter. The thermocouple amplifier 108 is also provided with additional temperature outputs from a dual temperature probe 111 which can be in the form of two probes for monitoring rectal temperatures. For example the two locations in the rectum may be utilized for measuring temperature by placing rectal tape having appropriate spacing as for example 2" between temperature probes to verify that there is no undue heating in the rectal area. The dual temperature probe 111 supplies temperature signals through line 112 to the thermocouple amplifier 108. The output from the thermocouple amplifier 108 is supplied to the RF output 107 to provide an input signal to the RF output 107 through a conductive path represented by the line 113. Thus the information supplied from the thermocouple amplifier carries information from four different sources in which two of the sources are thermocouples that are located on the insulating sleeves of the needle electrodes carried by the catheter which measures the temperature of the tissue immediately proximal to the needle electrodes and two additional thermocouples that are close to the base of the catheter or probe 11 and are utilized for measuring urethral temperatures. The line 116 from the RF output 107 to the catheter or probe 11 represents two independent RF channels for supplying radio frequency energy to the two separate probes of the catheter. The radio frequency power returns through the return pad 26 as indicated by the line 122. The RF output 107 also can be considered to be an analog signal processing block which performs some filtering, additional amplification and scaling of the thermocouple signals supplied on the line 113 and this information is supplied to the RFC board 106 through the line 126. The RFC board 106 also can be considered to be performing control algorithms for power generation for the apparatus. Thus the power output is controlled by the RFC board 106 which supplies a command to the RF output 107 to maintain the power output at that level. The line 131 connects the RFC board 106 to a block 132 which represents the primary display panel seven segment displays, backlighting and switches hereinbefore described. The line 131 represents an integrated signal and +5V. The foot pedal 21 is coupled to the RFC board 106 through a line 136.

Power is supplied to the RF generation and control section 103 from the instrument power section 102. First and second power supply units 151 and 152 are provided which supply +5, +12 and −12V power to the RFC board 106 through lines 153 and 154 respectively. In addition the power supply unit 151 supplies 24V power to the RF output 107 through line 156. Power is also supplied from the power supply unit 151 to the RF output through a line 156 which carries suitable power as for example 24V. It can be seen that the two power supply units 151 and 152 supply all of the different DC voltages which are required for the RF generation and control section. The power supply units 151 and 152 are of medical grade which meet conventional patient leakage requirements to prevent any possible patient electrocution.

Power is supplied to the power supply units 151 and 152 from a power entry module 166 which takes conventional 115V 60 cycle AC power which filters such power to remove current and power spikes. The power supply unit 152 is utilized for supplying +5 and +12V DC power through a line 166 and +5, +12 and −12V DC power through line 167 to the data display and recording section 104. The data display and recording section 104 includes a data control computer (DCC) 171 which controls the display of data. The DCC computer 171 includes a suitable processor such as a Pentium™ chip which is controlled by a suitable operating system represented by the block 172 and utilizing suitable operating system software such as Windows 95. The data control computer's operating system 172 forms a part of a DCC motherboard represented by the block 176. The DCC motherboard 176 also includes a minimum of 8-MB DRAM represented by the block 177 for the operating system. The 8-MB DRAM 177 contains 8-MB of nsec DRAM organized as two 1 MEG×23 SIMMs.

The DCC motherboard 176 also includes a 256-K byte cache SRAM 178. Also provided is a DCC BIOS ROM chip 179 which is provided to give standard interfacing capabilities with the Windows 95 operating system 172. The motherboard 176 also includes an IDE controller chip 181 which is a standard interface for a hard disk drive 188 and a FDD controller 182 which is a conventional floppy disk drive. The outputs from the controllers 181 and 182 are supplied by lines 186 and 187 to a hard disk drive 188 and a floppy disk drive 189 that are connected to the line 166 from the instrument power section 102.

The data display and recording section 104 also includes an integrated alpha keyboard 191 which represents the keyboard 79 and the touch pad 81 shown in FIG. 1 and is connected to the DCC motherboard 176 by two interfaces 192 and 193. The interface 192 is a PS/2 mouse port and includes signal and power whereas the other interface 193 includes a PS/2 Kbd interface which includes signal and power. The keyboard 191 includes a passive switch matrix 196 which is connected by an interface 197 to the touch pad 81.

The DCC motherboard 176 is connected by an IR/DA interface 201 to an IR transceiver module 202. The IR transceiver module 202 is coupled to a suitable printout means as for example a printer 203.

The DCC motherboard 176 is also connected by an ISA link 206 to an LCD video controller 207. The video controller 207 is connected by link 208 to LCD BL inverters 209. The inverter 209 is connected by a link 211 to an LCD backlight display 212.

From the foregoing it can be seen that the RF control computer i.e. the RFC board 106 utilizes a microcontroller which is supported by 32-K bytes of ROM and 8-K bytes of SRAM. It provides a direct control of the RF power supply 102. It receives user input via the primary display panel switch inputs hereinbefore described. The bi-directional parallel port 216 provides an 8 bit bi-directional parallel port capability with hardware handshaking for transfer to and from the DCC CPU 171 for storage and graphing. It acquires analog data from the thermocouple amplifier/signal conditioner module 108 and converts this information into digital form for processing and display. Also it provides an audible alarm (not shown). The display control computer 171 receives temperature, time, power and load impedance data from the RF control computer 106 and performs data management, processing, logging and display graphing functions.

Operation and use of the RF tissue ablation apparatus 11 in performing the method of the present invention may now be briefly described as follows. First let it be assumed that the apparatus has been prepared for performing a BPH procedure. Thus light energy is being supplied to the fitting 69. Liquid is being supplied to the fitting 71 and a vacuum has been placed in communication with the port 73. Also assume that there has been appropriate preparation of the male patient. The probe 61 is then introduced into the urethra of the penis of the male patient. It can be advanced through the urethra under direct vision through the eyepiece 67 and is continued to be advanced until the rounded tip 51 is appropriately located in the region of the prostate to be treated and which surrounds the urethra. This viewing is accomplished by having the optical viewing device 66 in its forwardmost position so that it views tissue distal of the rounded tip 51. As soon as the appropriate location in the prostate has been reached, the optical viewing device 66 can be retracted slightly so it is just proximal of the transparent rounded tip 51 so that deployment of the first and second needle assemblies 46 and 47 can be viewed. This deployment is accomplished by appropriate positioning of the sliders 58 and 61 to cause the distal extremities of the first and second needle electrodes 46 and 47 to project sidewardly or off axis through the urethral wall and into the selected lobe of the prostate to be treated. As soon as the needle electrode assemblies 46 and 47 have been advanced as far as desired into the prostate, the sliders 59 and 62 can be moved to cause retraction of the sleeves 53 surrounding the electrodes 52 to expose predetermined lengths of the electrodes within the prostatic tissue while still retaining the insulating sleeves so that they extend slightly beyond the urethral wall so as to protect the urethral wall from radio frequency ablation.

As soon as this has been accomplished and the physician is ready to apply radio frequency energy to start the ablation process, the physician operates the foot pedal 21 to cause the apparatus to enter a default mode following powering up to default to a standard option which typically is option No. 1 which will be displayed in the display next to the OPTION switch 97. Option No. 1 represents the standard nomogram. If the physician desires a different nomogram which is in the computer memory and represented by different option numbers, the physician can select the appropriate nomogram by operating the rocker switch 97 to select the appropriate option.

As soon as the appropriate option has been selected, the computer 71 runs through a sequence of checks to ascertain various temperatures being measured and the impedances being measured in order to ascertain whether the system is operating as expected. For example if the computer finds that there is an open thermocouple, an alarm will be sounded. On the other hand if the computer finds that everything is measured as contemplated within the nomogram, radio frequency energy is supplied to both channels to the first and second needle assemblies 46 and 47. As soon as this occurs, the rise timer starts counting down for example from a typical time of 4 minutes. The nomogram in the computer provides the temperatures which are to be achieved within the ablation of the prostate and the power is accordingly adjusted by the RFC 106 so that the target temperature is achieved. When the rise time goes to zero, the hold time will take over during which time the RFC 106 has continued to monitor the temperature of the prostate and continues to modulate the power being supplied to achieve the desired temperature and then to hold that desired temperature until the end of the ablation process. During the time that the RFC 106 is monitoring the power being supplied it is in fact monitoring the current and voltage of the power and thereby supplies the desired amount of power in accordance with the nomogram being utilized in the computer. At the same time that this is occurring, the impedance is calculated from the voltage and current measurements and the impedance is displayed on the control panel and is also graphically displayed on the LCD display panel 82 and which is displayed against time. As is well known to those skilled in the art, the impedance is obtained by dividing the voltage by the current and conversely that power is ascertained by multiplying voltage times current. The RF output board 107 includes the capability for calculating power and this is compared with current and voltage calculations to also ascertain power and if these two diverge dramatically, an alarm is sounded to indicate that the system is malfunctioning. Thus in the system of the present invention temperature, impedance and power are all being monitored continuously and are being utilized continuously for control purposes. In accordance with the procedure, the nomogram being utilized provides threshold values of impedance with respect to time which it is desired not be exceeded. Thus if at any time it is found that the impedance exceeds a threshold level, the RFC 106 cuts back the power supplied to a minimum allowed power as for example 1 watt and holds it there for a fixed amount of time as for example on the order of 5 seconds. If at that time the impedance has been reduced to below the threshold level, then the power being supplied is ramped up to approximately ½ the power that was being supplied at the time the threshold impedance was breached. Within 5 seconds after that, the power is again ramped up to ¾ of the exit power and then 5 seconds after that the algorithm being utilized in the nomogram is permitted to control the power back to its normal levels in accordance with the program and the nomogram. If a threshold level is again breached, the same procedure is undertaken.

Temperatures are monitored in a similar manner. For example if a temperature exceeds by 3° the nomogram temperature, the power being supplied is reduced to ½ of the power being supplied at that point in time and is held at that level for a period of 20 seconds, after which the nomogram controlling the computer permits the power level being supplied to return to normal. In this connection, a proportional temperature control can be utilized wherein when a temperature within 30 of a nomogram temperature is reached, the power being supplied can be reduced by a small amount until desired nomogram temperature or target temperature is reached to prevent overshooting. Conversely if at a time the measurement is below target temperature, the power being delivered can be increased slightly. When the ablation procedure has been completed, the radio frequency power is turned off and the apparatus is automatically reset to the default values with respect to rise, hold and target temperature.

If at any time the physician desires to go to a manual mode, the MODE SELECT pushbutton 92 is operated to cause the apparatus to go into the manual mode to cause the apparatus to immediately default to a 2 watt radio frequency power delivery on each of the first and second electrode assemblies 46 and 47. The power being supplied can then be increased or decreased manually and then set. Similarly, the target time can be set so that the procedure can be continued from where the automatic mode was terminated. This can continue until the rise and hold times selected have elapsed after which the apparatus will again return to the automatic mode and continue the automatic mode program from the time from which it was aborted to go to the manual mode. Thus it can be seen by utilization of the MODE SELECT button 92 it is possible to start in the automatic mode, go to the manual mode and then return to an automatic mode to permit completion of the ablation of the tissue automatically. The apparatus also has the capability of having the various parameters utilized for causing radio frequency ablation to be changed during an automatic mode procedure. Thus for example it is possible to change the rise time, the hold time and the target temperature during that time that radio frequency energy is being supplied to the tissue.

After an ablation procedure has been performed to create a lesion in one of the lateral lobes in the prostate, the first and second needle assemblies 46 and 47 can be retracted into the transparent rounded tip 51 by operation of the sliders 58, 59 and 61 and 62. Thereafter, the probe 16 can be rotated in the urethra to a position at another angle, as for example in the same lateral lobe and the needle assemblies 46 and 47 redeployed in the manner hereinbefore described and another lesion formed in the same lateral lobe.

The same procedure can be utilized in ablating tissue in the other lateral lobe of the prostate as for example in one or more locations in the other lateral lobe. If it is desired to perform an ablation in the median lobe of the prostate, this can be accomplished with the use of a single needle. The needle assemblies 46 and 47 are retracted and the probe 16 is rotated until the rounded tip 51 is disposed in the vicinity of the median lobe after which one of the first and second needle assemblies 46 and 47 can be deployed in the manner hereinbefore described to protrude through the urethral wall into the median lobe and the sleeve 53 retracted so that a predetermined amount of the electrode 52 is disposed within the median lobe with the sleeve still extending through the urethral wall so that the urethral wall is protected during ablation. As soon as the single needle has been positioned in the median lobe, the NEEDLE SELECT button 91 can be depressed to ensure that radio frequency energy is only supplied to the selected needle assembly as for example the second needle assembly 47. In a single needle operation, the apparatus typically would be in the automatic mode in which radio frequency energy is delivered in a programmed manner in the manner hereinbefore described to form the desired lesion in the median lobe. However it should be appreciated that at any time, a manual mode may be selected by immediately depressing the MODE SELECT button 92 after which manual operation of the type hereinbefore described can be undertaken.

After all of the desired ablation procedures have been performed in the prostate of the male, the first and second needle assemblies 46 and 47 can be retracted into the rounded tip 51 after which the probe 16 can be withdrawn from the urethra.

During the performance of the procedure as hereinbefore discussed, it is possible because of the design of the RF generator and control console 12 for a physician to control the entire procedure without use of an assistant to control the console 12. This is made possible because of the ready accessibility of the keyboard 79, the touch pad 81 and the backlit LED panel 82 as well as the large screen 86 provided so that the physician doing the procedure can readily observe the parameters being measured and displayed and can even make changes in the programming during the time a procedure is taking place. Thus it is possible for a physician to make changes on the fly, i.e., while a procedure is ongoing. This one person operation is facilitated by incorporating the computer and the radio frequency generator into a single case which in many respects is similar to a laptop computer in which the cover 78 can be lifted up to provide the liquid crystal display 86 to provide the necessary graphics during the procedure. The backlighted LED panel 82 with its highly visible indicia being displayed in a logical and very visible manner makes it possible for the physician to view the control console while he is actually doing the procedure. The physician can switch from automatic to manual control without starting over and even if the physician goes to automatic control, the apparatus will revert to the automatic mode after the period of time for manual control has elapsed, permitting the procedure to be completed in the automatic mode. The display utilized for the LED panel and for the liquid crystal display graphics and the use of color therewith facilitates transfer of information to the physician. An infrared transceiver module makes it possible to achieve patient isolation from external peripherals while providing the capability of sending the necessary data to generate hard copy reports and hard copy records. The hard disk provided as a part of the apparatus serves as a primary data archiving device which makes it possible to save the data from one procedure to another and to provide a permanent memory. Incorporating the floppy disk drive makes it possible to transfer data from the hard disk drive to the floppy disk drive to facilitate electronic copy archiving. The apparatus continuously monitors operating conditions and gives audible and visual alarms when out-of-limit parameters are detected. The construction of the RF generator and control console 12 is such that it can be utilized in a hospital environment by the use of a washable alphanumeric input keyboard. The display control computer displays, measures and sets values and permits manipulation of these values only. It is not involved in the control of the apparatus. Rather the control of the apparatus and the display of important procedure parameters are managed by the RF control computer.

What is claimed:

1. A radio frequency tissue ablation apparatus for use on a horizontal support surface in connection with a medical procedure on a patient comprising a portable carrying case having a carrying handle, the portable carrying case being adapted to rest upon the horizontal surface, the portable carrying case having a cover with an inner surface and being movable between a generally vertical open position and a generally horizontal closed position when the portable carrying case is resting on the horizontal support surface, the portable carrying case having a keyboard and a primary display panel disposed adjacent the keyboard underlying the cover when the cover is in a closed position and being accessible visually and physically when the cover is in an open position, said primary display panel including a plurality of groups of indicia and a plurality of switches associated with at least certain of the groups of indicia for establishing criteria for those certain groups of indicia, said primary display panel including an additional switch for selecting manual or automatic operation, a graphic display panel carried by the inner surface of the cover, electrical circuitry including a radio frequency generator and a control computer disposed within the portable carrying case and coupled to said keyboard, said primary display panel and said graphic display panel, said portable carrying case having a plurality of ports accessible externally in communication with the electrical circuitry in the portable carrying case and a probe coupled to one of the ports carrying an electrode adapted to penetrate tissue.

2. Apparatus as in claim 1 wherein said primary display panel has legends overlying the groups of indicia and wherein said primary display panel is backlit.

3. Apparatus as in claim 1 wherein said primary display panel is inclined at an angle with respect to the keyboard to improve visibility so that a single person can perform an ablation procedure while operating the controls.

4. Apparatus as in claim 1 wherein said electrical circuitry includes impedance measuring means for monitoring the impedance in the tissue being ablated and including means for ascertaining when a predetermined impedance in the tissue has been reached and means for automatically reducing the radio frequency power applied to the electrode without terminating the power to the electrical circuitry when the predetermined impedance has been reached.

5. Apparatus as in claim 4 wherein said electrical circuitry includes means for applying radio frequency power at a level to avoid creation of a high impedance condition after a predetermined impedance has been reached.

6. Apparatus as in claim 4 wherein said electrical circuitry includes means for permitting the predetermined impedance to prevail for only a short period of time.

7. Apparatus as in claim 4 wherein said impedance measuring means includes means for calculating impedance and displaying impedance measured on the graphic display panel with respect to time.

8. Apparatus as in claim 1 together with a foot pedal connected to one of the ports of the portable carrying case for controlling certain operations of the electrical circuitry.

9. Apparatus as in claim 1 together with a grounding pad adapted to be placed in contact with the patient and connected to one of the ports of the portable carrying case.

10. Apparatus as in claim 1 together with a touch pad mounted in the portable carrying case adjacent the keyboard for supplying information to the control computer.

11. A method for ablating tissue of a patient in a medical procedure by the use of a portable carrying case adapted to rest upon a horizontal support surface, the portable carrying case having a cover with an inner surface and being movable between a generally vertical open position and a generally horizontal closed position when the carrying case is resting on the horizontal support surface, the carrying case having a keyboard and a primary display panel disposed adjacent the keyboard underlying the cover when the cover is in a closed position and being accessible visually and physically when the cover is in an open position, a graphic display panel carried by the inner surface of the cover, said primary display panel including a plurality of groups of indicia and a plurality of switches associated with at least certain of the groups of indicia for establishing criteria for those certain groups of indicia, electrical circuitry including a radio frequency generator and a control computer disposed within the portable carrying case and coupled to the keyboard, the primary display panel and to the graphic display panel and by the use of a probe carrying an electrode adapted to penetrate tissue, said primary display panel having control switches for selecting automatic or manual operation, the method comprising setting parameters for the medical procedure utilizing the keyboard and said switches, performing the medical procedure to supply radio frequency energy from the radio frequency generator to the electrode of the probe to cause ablation of tissue in the patient while operating the switches and alternatively selecting manual or automatic operation for supplying radio frequency energy to the electrode during the medical procedure.

12. A method as in claim 11 together with the step of ascertaining the impedance in the tissue being ablated and ascertaining when a predetermined impedance has been reached and automatically reducing the radio frequency power applied to the electrode when the predetermined impedance has been reached without terminating power to the electrical circuitry.

13. A method as in claim 12 together with the step of applying radio frequency power at a level to avoid creating a high impedance condition after the predetermined impedance has been reached.

14. A method as in claim 12 together with the step of permitting a high impedance condition to prevail for only a short period of time.

15. A radio frequency tissue ablation apparatus for use on a horizontal support surface in connection with a medical procedure on a patient comprising a portable carrying case having a carrying handle, the portable carrying case being adapted to rest upon the horizontal surface, the portable carrying case having a cover with an inner surface and being movable through an angle of at least approximately 90° between an open position and a generally horizontal closed position when the portable carrying case is resting on the horizontal support surface, the portable carrying case having a primary display panel underlying the cover when the cover is in a closed position and being accessible visually and physically when the cover is in an open position, said primary display panel including a plurality of groups of indicia and a plurality of switches associated with at least certain of the groups of indicia for establishing criteria for those certain groups of indicia, said primary display panel including an additional switch for selecting manual or automatic operation, electrical circuitry including a radio frequency generator and a control computer disposed within the portable carrying case and coupled to said primary display panel, said portable carrying case having a plurality of ports accessible externally in communication with the electrical circuitry in the portable carrying case and a probe coupled to one of the ports carrying an electrode adapted to penetrate tissue.

16. Apparatus as in claim 15 wherein said primary display panel has legends overlying the groups of indicia and wherein said primary display panel is backlit.

17. Apparatus as in claim 15 wherein said primary display panel is inclined at an angle with respect to horizontal when the portable carrying case is resting on the horizontal support surface to improve visibility so that a single person can perform an ablation procedure while operating the controls.

18. Apparatus as in claim 15 wherein said electrical circuitry includes impedance measuring means for monitoring the impedance in the tissue being ablated and including means for ascertaining when a predetermined impedance in the tissue has been reached and means for automatically reducing the radio frequency power applied to the electrode without terminating the power to the electrical circuitry when the predetermined impedance has been reached.

19. Apparatus as in claim 18 wherein said electrical circuitry includes means for applying radio frequency power at a level to avoid creation of a high impedance condition after a predetermined impedance has been reached.

20. Apparatus as in claim 15 together with a foot pedal connected to one of the ports of the portable carrying case for controlling certain operations of the electrical circuitry.

21. Apparatus as in claim 15 together with a grounding pad adapted to be placed in contact with the patient and connected to one of the ports of the portable carrying case.

* * * * *